United States Patent [19]

Barth

[11] 4,256,733

[45] Mar. 17, 1981

[54] ACETOXYMETHYL PENAM COMPOUNDS AS β-LACTAMASE INHIBITORS

[75] Inventor: Wayne E. Barth, East Lyme, Conn.

[73] Assignee: Pfizer Inc., New York, N.Y.

[21] Appl. No.: 79,127

[22] Filed: Sep. 26, 1979

[51] Int. Cl.³ .................... C07D 499/00; A61K 31/43
[52] U.S. Cl. ............................ 424/114; 260/245.2 R; 424/271
[58] Field of Search ............................... 424/271, 114; 260/245.2

[56] References Cited

FOREIGN PATENT DOCUMENTS 2824535 12/1978 Fed. Rep. of Germany .
1072108 6/1967 United Kingdom .

OTHER PUBLICATIONS

Chakovskaya et al., Antibiotiki 13, 155 (1968).
Barton et al., JCS (London) Part D, 1683 (1970).
Ibid Part C, 3540 (1971).
Morin et al., JACS 91, 1401 (1969).
Hauser et al., Helvetica Chimica Acta 50, 1327 (1967).
Vanderhaeghe et al., Recent Advances in the Chemistry of β-Lactam Antibiotics, J. Elus Editor, The Chemical Society (London) Special Publication No. 28, Chap. 32, pp. 304–313.

*Primary Examiner*—Nicholas S. Rizzo
*Attorney, Agent, or Firm*—Francis X. Murphy; Charles J. Knuth; J. Trevor Lumb

[57] ABSTRACT

2β-Acetoxymethyl-2α-methyl-(5R)penam-3α-carboxylic acid 1,1-dioxide, pharmaceutically-acceptable salts thereof and esters thereof readily hydrolyzable in vivo; pharmaceutical compositions containing 2β-acetoxymethyl-2α-methyl-(5R)penam-3α-carboxylic acid 1,1-dioxide or salt or ester thereof; and method of enhancing the effectiveness of a β-lactam antibiotic using 2β-acetoxymethyl-2α-methyl-(5R)penam-3α-carboxylic acid 1,1-dioxide or salt or ester thereof.

22 Claims, No Drawings

ACETOXYMETHYL PENAM COMPOUNDS AS β-LACTAMASE INHIBITORS

BACKGROUND OF THE INVENTION

One of the most well-known and widely-used classes of antibacterial agents is the class known as the β-lactam antibiotics. These compounds are characterized in that they have a nucleus consisting or a 2-azetidinone (β-lactam) ring fused to either a thiazolidine or a dihydro-1,3-thiazine ring. When the nucleus contains a thiazolidine ring, the compounds are usually referred to generically as penicillins, whereas when the nucleus contains a dihydrothiazine ring, the compounds are referred to as cephalosporins. Typical examples of penicillins which are commonly used in clinical practice are benzylpenicillin (penicillin G), phenoxymethylpenicillin (penicillin V), ampicillin and carbenicillin; typical examples of common cephalosporins are cephalothin, cephalexin and cefazolin.

However, despite the wide use and wide acceptance of the β-lactam antibiotics as valuable chemotherapeutic agents, they suffer from the major drawback that certain members are not active against certain microorganisms. It is thought that in many instances this resistance of a particular microorganism to a given β-lactam antibiotic results because the microorganism produces a β-lactamase. The latter substances are enzymes which cleave the β-lactam ring of penicillins and cephalosporins to give products which are devoid of antibacterial activity. However, certain substances have the ability to inhibit β-lactamases, and when a β-lactamase inhibitor is used in combination with a penicillin or cephalosporin it can increase or enhance the antibacterial effectiveness of the penicillin or cephalosporin against certain microorganisms. It is considered that there is an enhancement of antibacterial effectiveness when the antibacterial activity of a combination of a β-lactamase inhibiting substance and a β-lactam antibiotic is significantly greater than the sum of the antibacterial activities of the individual components.

Thus, according to the invention, there are provided certain new chemical compounds which are potent inhibitors of microbial β-lactamases. More specifically, these new chemical compounds are 2β-acetoxymethyl-2α-methyl-(5R)-penam-3α-carboxylic acid 1,1-dioxide, pharmaceutically-acceptable salts thereof and esters thereof readily hydrolyzable in vivo. Additionally, there is provided a method for enhancing the effectiveness of β-lactam antibiotics using said new chemical compounds, and pharmaceutical compositions comprising said new chemical compounds. Yet further, according to the invention, there are provided certain compounds useful as intermediates to said novel β-lactamase inhibitors.

Several penicillin derivatives were tested as potential β-lactamase inhibitors by Chaikovskaya et al., *Antibiotiki*, 13, 155 (1968); benzylpenicillin 1,1-dioxide was found to be inactive. Penam compounds having an acetoxymethyl group at the 2-position are disclosed by Morin et al., *Journal of the American Chemical Society*, 91, 1401 (1969), and by Barton et al., *Journal of the Chemical Society* (London) Part D, 1683 (1970); ibid. Part C, 3540 (1971). Deamination of 6-aminopenicillanic acid in the presence of acetic acid gives 6α-acetoxypenicillanic acid, which was converted into its methyl ester using diazomethane (Hauser and Sigg, *Helvetica Chimica Acta*, 50, 1327 [1967]). Penicillanic acid is disclosed in British Pat. No. 1,072,108.

West German Offenlegungsschrift No. 2,824,535, published Dec. 14, 1978, and Iranian Pat. No. 19,601, granted July 12, 1978, disclose penicillanic acid 1,1-dioxide, and esters thereof readily hydrolyzable in vivo, as antibacterial agents and as β-lactamase inhibitors. Penicillanic acid 1,1-dioxide and esters thereof readily hydrolyzable in vivo increase the antibacterial effectiveness of certain penicillin and cephalosporin compounds against certain bacteria.

SUMMARY OF THE INVENTION

According to the invention, there are provided novel penam compounds of the formula

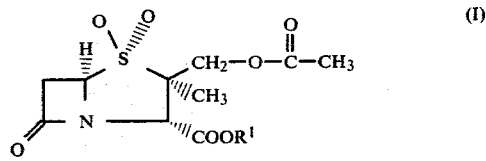

and the pharmaceutically-acceptable base salts thereof, wherein $R^1$ is selected from the group consisting of hydrogen and ester-forming residues readily hydrolyzable in vivo. Said compounds of formula I are useful as β-lactamase inhibitors, and they increase the effectiveness of several β-lactam antibiotics against many β-lactamase producing microorganisms.

Also, according to the invention, there are provided pharmaceutical compositions which comprise a compound of formula I, or a pharmaceutically-acceptable base salt thereof, and a pharmaceutically-acceptable carrier.

Also, according to the invention there is provided a method of increasing the effectiveness of a β-lactam antibiotic in a human subject, which comprises coadministering, with said β-lactam antibiotic, to said human subject, a β-lactam antibiotic effectiveness increasing amount of a compound of formula I, or a pharmaceutically-acceptable base salt thereof.

Still further, according to the invention, there are provided novel penam compounds of the formula

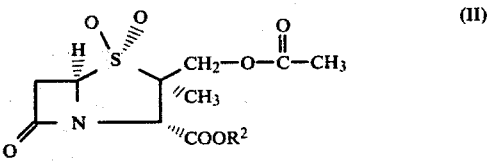

wherein $R^2$ is a conventional penicillin carboxy protecting group. Said compounds of formula II are useful as chemical intermediates to the compounds of formula I.

Yet further, according to the invention there are provided novel penam compounds of the formula

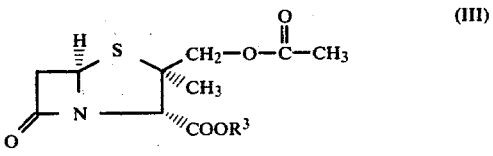

and the base salts thereof, wherein $R^3$ is selected from the group consisting of hydrogen, ester-forming residues readily hydrolyzable in vivo, and conventional penicillin carboxy protecting groups. Said compounds of formula III are useful as intermediates.

The term "ester-forming residues readily hydrolyzable in vivo" is here intended to refer to non-toxic ester residues which are rapidly cleaved in human blood or tissue, to release the corresponding free acid. Preferred examples of such readily hydrolyzable ester-forming residues which can be used for $R^1$ or $R^3$ are 3-phthalidyl, 4-crotonolactonyl, γ-butyrolacton-4-yl,

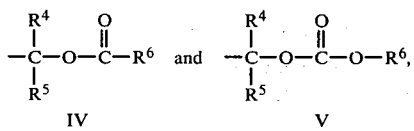

wherein $R^4$ and $R^5$ are each selected from the group consisting of hydrogen and methyl, and $R^6$ is alkyl having from 1 to 5 carbon atoms. Especially preferred examples of individual readily hydrolyzable esterforming residues are pivaloyloxymethyl (the group of formula IV, wherein $R^4$ and $R^5$ are each hydrogen and $R^6$ is t-butyl) and 1-(ethoxycarbonyloxy)ethyl (the group of formula V, wherein $R^4$ is hydrogen, $R^5$ is methyl and $R^6$ is ethyl). Typical conventional penicillin carboxy protecting groups are benzyl and substituted benzyl, e.g., 4-nitrobenzyl.

DETAILED DESCRIPTION OF THE INVENTION

The compounds of this invention are the compounds of formulae I, II and III. Throughout this specification these compounds are named as derivatives of penam, which has been defined by Sheehan et al., *Journal of the American Chemical Society*, 75, 3293 (1953), as referring to the structure:

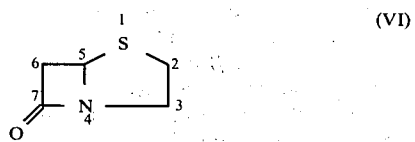

Although the term "penam" does not specify the stereochemistry at C-5 in the structure VI, all the compounds of the present invention are derived from naturally-occurring penicillin compounds. Accordingly, using the Cahn-Ingold-Prelog system of denoting stereochemistries, the compounds of this invention have the (R)-configuration at C-5, so they are named as derivatives of (5R)penam. See further, Cahn and Ingold, *Journal of the Chemical Society* (London), 612 (1951) and Cahn, Ingold and Prelog, *Experientia*, 12, 81 (1956).

When depicting derivatives of the structure VI, the bicyclic ring system is understood to substantially be in the plane of the paper. Broken line attachment of a group to the ring system VI indicates that the group is attached from below the plane of the paper, and such a group is said to be in the α-configuration. Conversely, solid line attachment of a group to the ring system VI indicates that the group is attached from above the plane of the paper, and this latter configuration is referred to as the β-configuration.

As indicated hereinbefore, the compounds of this invention are the compounds of formulae I, II and III, and base salts thereof. When $R^1$ or $R^3$ is an esterforming residue readily hydrolyzable in vivo in a compound of formula I or III, it is a grouping which is notionally derived from an alcohol of the formula $R^1$—OH or $R^3$—OH, such that the moiety $COOR^1$ or $COOR^3$ is readily cleaved in vivo to liberate a free carboxy group (COOH). That is to say, $R^1$ or $R^3$ is a group of the type that when a compound of formulae I or III, wherein $R^1$ or $R^3$ is an ester-forming residue readily hydrolyzed in vivo, is exposed to human blood or tissue, the compound of formula I or III, wherein $R^1$ or $R^3$ is hydrogen, is readily produced. Such groups for $R^1$ or $R^3$ are well-known in the penicillin art. In most instances they improve the absorption characteristics of the penicillin compound. Additionally, $R^1$ or $R^3$ should be of such a nature that it imparts pharmaceutically-acceptable properties to a compound of formulae I or III and it liberates pharmaceutically-acceptable fragments when cleaved in vivo.

As indicated above, ester-forming residues readily hydrolyzable in vivo are well-known and are readily identified by those skilled in the penicillin art. See, for example, West German Offenlegungsschrift No. 2,517,316. Typical examples of such groups are 3-phthalidyl, 4-crotonolactonyl, gamma-butyrolacton-4-yl and groups of the formula

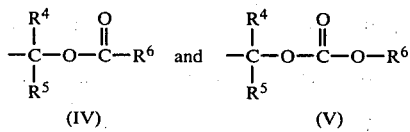

wherein $R^4$ and $R^5$ are each selected from the group consisting of hydrogen and methyl and $R^6$ is alkyl having from 1 to 5 carbon atoms. However, preferred groups for $R^1$ are alkanoyloxymethyl having from 3 to 7 carbon atoms and 1-(alkoxycarbonyloxy)ethyl having from 4 to 7 carbon atoms.

As indicated hereinbefore, the β-lactamase inhibitors of this invention are the compounds of the formula I, wherein $R^1$ is selected from the group consisting of hydrogen and ester-forming residues readily hydrolyzable in vivo. These compounds can be prepared by oxidation of the corresponding compound of formula III, wherein $R^3$ is selected from the group consisting of hydrogen and ester-forming residues readily hydrolyzable in vivo. Additionally, the compound of formula I, wherein $R^1$ is hydrogen can be prepared by oxidation of a compound of formula III, wherein $R^3$ is a conventional penicillin carboxy protecting group, to give a compound of the formula II, wherein $R^2$ is a conventional penicillin carboxy protecting group, followed by removal of the protecting group.

For the purpose of oxidizing a compound of the formula III, wherein $R^3$ is hydrogen or an ester-forming residue readily hydrolyzable in vivo, to the corresponding compound of formula I, and oxidizing a compound of formula III, wherein $R^3$ is a protecting group, to the corresponding compound of formula II, a wide variety of oxidants known in the art for the oxidation of sulfides to sulfones can be used. However, particularly convenient reagents are metal permanganates, such that alkali metal permanganates and the alkaline earth metal permanganates, and organic peroxy acids, such as organic peroxycarboxylic acids. Convenient individual reagents are sodium permanganate, potassium permanganate, 3-chloroperbenzoic acid and peracetic acid.

When a compound of the formula III, wherein $R^3$ is selected from the group consisting of hydrogen, ester-forming residues readily hydrolyzable in vivo and conventional penicillin carboxy protecting groups, is oxidized to the corresponding compound of the formula I or II using a metal permanganate, the reaction is usually carried out by treating the compound of the formula III with from about 0.5 to about 5 molar equivalents of the permanganate and preferably about 1 molar equivalent of the permanganate, in an appropriate solvent system. An appropriate solvent system is one that does not adversely interact with either the starting material or the product, and water is commonly used. If desired, a co-solvent which is miscible with water but will not interact with the permanganate, such as tetrahydrofuran, can be added. The reaction is normally carried out at a temperature in the range from about −20° to about 50° C., and preferably at about 0° C. At about 0° C. the reaction is normally substantially complete within a short period, e.g. within one hour. Although the reaction can be carried out under neutral basic or acidic conditions, it is preferable to operate under substantially neutral conditions in order to avoid decomposition of the β-lactam ring system of the compound of the formula I or II. Indeed, it is often advantageous to buffer the pH of the reaction medium in the vicinity of neutrality. The product is recovered by conventional techniques. Any excess permanganate is usually decomposed using sodium bisulfite, and then if the product is out of solution, it is recovered by filtration. It is separated from manganese dioxide by extracting it into an organic solvent and removing the solvent by evaporation. Alternatively, if the product is not out of solution at the end of the reaction, it is isolated by the usual procedure of solvent extraction.

When a compound of the formula III, wherein $R^3$ is selected from the group consisting of hydrogen, ester-forming residues readily hydrolyzable in vivo, and conventional penicillin carboxy protecting groups, is oxidized to the corresponding compound of the formula I or II using an organic peroxy acid, e.g., a peroxycarboxylic acid, the reaction is usually carried out by treating the compound of the formula III with from about 2 to about 5 molar equivalents, and preferably about 2.2 equivalents of the oxidant in a reaction-inert organic solvent. Typical solvents are chlorinated hydrocarbons, such as dichloromethane, chloroform and 1,2-dichloroethane; and ethers, such as diethyl ether, tetrahydrofuran and 1,2-dimethoxyethane. The reaction is normally carried out at a temperature of from about −20° to about 50° C., and preferably at about 25° C. At about 25° C. reaction times of about 2 to about 16 hours are commonly used. The product is normally isolated by removal of the solvent by evaporation in vacuo. The product can be purified by conventional methods, well-known in the art.

When oxidizing a compound of the formula III to a compound of the formula I or II using an organic peroxy acid, it is sometimes advantageous to add a catalyst such as a manganese salt, e.g. manganic acetylacetonate.

When the compound of the formula I, wherein $R^1$ is hydrogen is obtained by removal of the protecting group $R^2$ from a compound of the formula II, wherein $R^2$ is a penicillin carboxy protecting group, the identity of the carboxy protecting group is not critical. The only requirements for the carboxy protecting group are that: (i) it must be stable during oxidation of the compound of formula III; and (ii) it must be removable from the compound of formula II, using conditions under which the β-lactam remains substantially intact. Typical examples which can be used are the tetrahydropyranyl group, the benzyl group, substituted benzyl groups (e.g. 4-nitrobenzyl), the benzhydryl group, the 2,2,2-trichloroethyl group, the t-butyl group and the phenacyl group. See further: U.S. Pat. Nos. 3,632,850 and 3,197,466; British Pat. No. 1,041,985, Woodward et al., *Journal of the American Chemical Society*, 88, 852 (1966); Chauvette, *Journal of Organic Chemistry*, 36, 1259 (1971); Sheehan et al., *Journal of Organic Chemistry*, 29, 2006 (1964); and "Cephalosporin and Penicillins, Chemistry and Biology," edited by H. E. Flynn, Academic Press, Inc., 1972.

The penicillin carboxy protecting group is removed in conventional manner for that group, having due regard for the lability of the β-lactam ring system. When $R^2$ is a benzyl, substituted benzyl or benzhydryl group, it can be removed conveniently by catalytic hydrogenolysis. In this case, a solution of the compound of the formula II, wherein $R^2$ is benzyl, substituted benzyl or benzhydryl, is stirred or shaken under an atmosphere of hydrogen, or hydrogen mixed with an inert diluent such as nitrogen or argon, in the presence of a catalytic amount of palladium-on-carbon catalyst. Convenient solvents for this hydrogenolysis are lower-alkanols, such as methanol; ethers such as tetrahydrofuran and dioxan; low molecular weight esters, such as ethyl acetate and butyl acetate; water; and mixtures of these solvents. However, it is usual to choose conditions under which the starting material is soluble. The hydrogenolysis is usually carried out at room temperature and at a pressure from about 0.5 to about 5 kg/cm². The catalyst is usually present in an amount from about 10 percent by weight based on the starting material up to an amount equal in weight to the starting material, although larger amounts can be used. The reaction commonly takes about one hour, after which the compound of the formula I, wherein $R^1$ is hydrogen, is recovered simply by filtration followed by removal of the solvent in vacuo.

The compounds of formula III, wherein $R^3$ is selected from the group consisting of ester-forming residues readily hydrolyzable in vivo and conventional penicillin carboxy protecting groups are prepared from a compound selected from the group consisting of

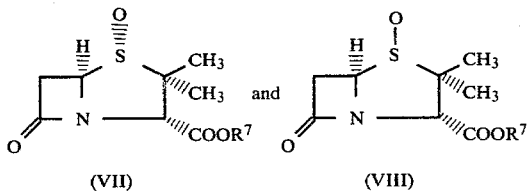

or a mixture thereof, wherein $R^7$ is selected from the group consisting of ester-forming residues readily hydrolyzable in vivo and conventional penicillin carboxy protecting groups.

The conversion of a compound of formula VII or VIII, or mixture thereof, into a compound of formula III is normally carried out by treating the compound of formula VII or VIII, or mixture thereof, with acetic anhydride. This conversion is normally carried out by heating the compound of formula VII or VIII, or mixture thereof, with a large excess of acetic anhydride in an inert solvent. Usually, from about a 20-fold to a 100-fold molar excess of acetic anhydride is used. The inert solvent used for this transformation is usually a relatively non-polar solvent, which has no reactive functional groups, and which has a boiling point greater than about 80° C. Typical solvents which are used are aromatic hydrocarbons, such as toluene, xylene and naphthalene; chlorinated aromatic hydrocarbons such as chlorobenzene; aromatic ethers such as anisole, phenetole and diphenyl ether; and alphatic hydrocarbons such as decalin. The reaction is normally run at a temperature in the range from about 80° to about 130° C., and preferably at about 110° to 115° C. At a temperature of about 110° C., the reaction commonly takes about one hour substantially to reach completion. The product is isolated by standard techniques for $\beta$-lactam compounds. The product can be purified by standard techniques for $\beta$-lactam compounds, if desired, or it can be used directly without purification. The conventional penicillin carboxy protecting groups used for $R^7$ are the same groups that were described earlier for use in the oxidation of a compound of formula III to a compound of formula II. Particularly useful groups are benzyl, substituted benzyl and benzhydryl, especially benzyl.

The compound of formula III, wherein $R^3$ is hydrogen, is obtained from a compound of formula III, wherein $R^3$ is a conventional penicillin carboxy protecting group, by removal of the protecting group. The protecting group is removed in the normal manner for the particular protecting group being used. For example, benzyl, substituted benzyl and benzhydryl are conveniently removed by hydrogenolysis using the conditions described earlier for removal of these groups from a compound of formula II.

The compounds of formulae VII and VIII are known compounds which are prepared using the published procedures (West German Offenlegungsschrift No. 2,824,535).

The compounds of formula I, wherein $R^1$ is an ester-forming residue readily hydrolyzable in vivo can be prepared directly from the corresponding compound of formula I wherein $R^1$ is hydrogen, by esterification. The specific method chosen will depend naturally upon the precise structure of the ester-forming residue, but an appropriate method will be readily selected by one skilled in the art. In the case wherein $R^1$ is selected from the group consisting of 3-phthalidyl, 4-crotonolactonyl, $\gamma$-butyrolacton-4-yl and groups of the formula IV and V, wherein $R^4$, $R^5$ and $R^6$ are as defined previously, they can be prepared by alkylation of the appropriate compound of formula I, wherein $R^1$ is hydrogen, with a 3-phthalidyl halide, a 4-crotonolactonyl halide, a $\gamma$-butyrolacton-4-yl halide or a compound of the formula

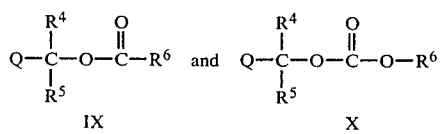

wherein Q is halo, and $R^4$ $R^5$ and $R^6$ are as previously defined. The terms "halide" and "halo" are intended to mean derivatives of chlorine, bromine and iodine. The reaction is conveniently carried out by dissolving a salt of said compound of formula I, wherein $R^1$ is hydrogen, in a suitable, polar, organic solvent, such as N,N-dimethylformamide, and then adding about one molar equivalent of the halide. When the reaction has proceeded essentially to completion, the product is isolated by standard techniques. It is often sufficient simply to dilute the reaction medium with an excess of water, and then extract the product into a water-immiscible organic solvent and then recover same by solvent evaporation. Salts of the starting material which are commonly used are alkali metal salts, such as sodium and potassium salts, and tertiary amine salts, such as triethylamine, ethyldiisopropylamine, N-ethylpiperidine, N,N-dimethyl-aniline and N-methylmorpholine salts. The reaction is run at a temperature in the range from about 0° to 100° C., and usually at about 25° C. The length of time needed to reach completion varies according to a variety of factors, such as the concentration of the reactants and the reactivity of the reagents. Thus, when considering the halo compound, the iodide reacts faster than the bromide, which in turn reacts faster than the chloride. In fact, it is sometimes advantageous, when utilizing a chloro compound, to add up to one molar equivalent of an alkali metal iodide. This has the effect of speeding up the reaction. With full regard for the foregoing factors, reaction times of from about 1 to about 24 hours are commonly used.

The compounds of formula I and III, wherein $R^1$ and $R^3$, respectively, are hydrogen, are acidic and they will form salts with basic agents. These salts can be prepared by standard techniques, such as contacting the acidic and basic components, usually in a stoichiometric ratio, in an aqueous, non-aqueous or partially aqueous medium, as appropriate. They are then recovered by filtration, by precipitation with a non-solvent followed by filtration, by evaporation of the solvent, or in the case of aqueous solutions, by lyophilization, as appropriate. Basic agents which are suitably employed in salt formation belong to both the organic and inorganic types, and they include ammonia, organic amines, alkali alkoxides, as well as alkaline earth metal hydroxides, carbonates, hydrides and alkoxides. Representative examples of such bases are primary amines, such as n-propylamine, n-butylamine, aniline, cyclohexylamine, benzylamine and octylamine; secondary amines, such as diethylamine, morpholine, pyrrolidine and piperidine; tertiary amines, such as triethylamine, N-ethylpiperidine, N-methylmorpholine and 1,5-diazabicyclo[4.3.0]non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; bicarbonates, such as sodium bicarbonate, and potassium bicarbonate; and alkali metal salts of long-chain fatty acids, such as sodium 2-ethylhexanoate.

The compound of formula I, wherein $R^1$ is hydrogen is a potent inhibitor of microbial $\beta$-lactamases, and it will increase the antibacterial effectiveness of $\beta$-lactam antibiotics (penicillins and cephalosporins) against many microorganisms which produce a $\beta$-lactamase, both in vitro and in vivo. The compounds of formula I, wherein $R^1$ is an ester-forming residue readily hydrolyzable in vivo are potent inhibitors of microbial $\beta$-lactamases, and they will increase the antibacterial effectiveness of $\beta$-lactam antibiotics (penicillins and cephalosporins) against many microorganisms which produce a $\beta$-lactamase, in vivo. The manner in which the compound of the formula I, wherein $R^2$ is hydrogen, increases the effectiveness of a $\beta$-lactam antibiotic in vitro can be appreciated by reference to experiments in which the MIC (Minimum Inhibitory Concentration) of a given antibiotic alone, and said compound of the formula I alone, are measured. These MIC's are then compared with the MIC values obtained with a combination of the given antibiotic and the compound of the formula I. When the antibacterial potency of the combination is significantly greater than would have been predicted from the potencies of the individual compounds, this is considered to constitute enhancement of activity. The MIC values of combinations are measured using the method described by Barry and Sabath in "Manual of Clinical Microbiology", edited by Lenette, Spaulding and Truant, 2nd edition, 1974, American Society for Microbiology.

The compounds of the formula I, and salts thereof, enhance the antibacterial effectiveness of β-lactam antibiotics in vivo, i.e., they lower the amount of antibiotic which is needed to protect mice against an otherwise lethal inoculum of certain β-lactamase producing bacteria.

The ability of the compounds of the formula I, and salts thereof, to enhance the effectiveness of a β-lactam antibiotic against β-lactamase-producing bacteria makes them valuable for co-administration with β-lactam antibiotics in the treatment of bacterial infections in humans. In the treatment of a bacterial infection, said compound of the formula I can be comingled with the β-lactam antibiotic, and the two agents thereby administered simultaneously. Alternatively, said compound of the formula I can be administered as a separate agent during a course of treatment with a β-lactam antibiotic. In some instances it will be advantageous to pre-dose the subject with the compound of the formula I before initiating treatment with a β-lactam antibiotic.

When using a compound of formula I, or a salt thereof to enhance the effectiveness of a β-lactam antibiotic in a human subject, it can be administered alone, or it can be mixed with pharmaceutically acceptable carriers or diluents. It can be administered orally or parenterally, i.e. intramuscularly, subcutaneously or intraperitoneally. The carrier or diluent is chosen on the basis of the intended mode of administration. For example, when considering the oral mode of administration, a compound of this invention of formula I can be used in the form of tablets, capsules, lozenges, troches, powders, syrups, elixirs, aqueous solutions and suspensions, and the like, in accordance with standard pharmaceutical practice. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights from 2,000 to 4,000. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous and intravenous use, sterile solutions of the active ingredient are usually prepared, and the pH of the solutions are suitably adjusted and buffered. For intravenous use, the total concentration of solutes should be controlled to render the preparation isotonic. A pharmaceutical composition containing a compound of this invention will normally contain from about 20 to about 95 percent by weight of the compound of formula I.

When using a compound of formula I in combination with another β-lactam antibiotic, the compound can be administered orally or parenterally, i.e. intramuscularly, subcutaneously or intraperitoneally. Although the prescribing physician will ultimately decide the dosage to be used in a human subject, the ratio of the daily dosages of the penam of this invention and the β-lactam antibiotic will normally be in the range from about 1:3 to 3:1. Additionally, when using a compound of this invention in combination with another β-lactam antibiotic, the daily oral dosage of each component will normally be in the range from about 10 to about 200 mg per kilogram of body weight and the daily parenteral dosage of each component will normally be about 10 to about 400 mg per kilogram of body weight. These figures are illustrative only, however, and in some cases it may be necessary to use dosages outside these limits.

Typical β-lactam antibiotics with which a compound of formula I or salts or esters readily hydrolyzable in vivo can be co-administered are:
6-(2-phenylacetamido)penicillanic acid,
6-(2-phenoxyacetamido)penicillanic acid,
6-(2-phenylpropionamido)penicillanic acid,
6-(D-2-amino-2-phenylacetamido)penicillanic acid,
6-(D-2-amino-2-[4-hydroxyphenyl]acetamido)penicillanic acid,
6-(D-2-amino-2-[1,4-cyclohexadienyl]acetamido)penicillanic acid,
6-(1-aminocyclohexanecarboxamido)penicillanic acid,
6-(2-carboxy-2-phenylacetamido)penicillanic acid,
6-(2-carboxy-2-[3-thienyl]acetamido)penicillanic acid,
6-(D-2-[4-ethylpiperazin-2,3-dione-1-carboxamido]-2-phenylacetamido)penicillanic acid,
6-(D-2-[4-hydroxy-1,5-naphthyridine-3-carboxamido]-2-phenylacetamido)penicillanic acid,
6-(D-2-sulfo-2-phenylacetamido)penicillanic acid,
6-(D-2-sulfoamino-2-phenylacetamido)penicillanic acid,
6-(D-2-[imidazolidin-2-one-1-carboxamido]-2-phenylacetamido)penicillanic acid,
6-(D-[3-methylsulfonylimidazoline-2-one-1-carboxamido]-2-phenylacetamido)penicillanic acid,
6-([hexahydro-1H-azepin-1-yl]methyleneamino)penicillanic acid,
acetoxymethyl 6-(2-phenylacetamido)penicillanate,
acetoxymethyl 6-(D-2-amino-2-phenylacetamido)penicillanate,
acetoxymethyl 6-(D-2-amino-2-[4-hydroxyphenyl]acetamido)penicillanate,
pivaloyloxymethyl 6-(2-phenylacetamido)penicillanate,
pivaloyloxymethyl 6-(D-2-amino-2-phenylacetamido)penicillanate,
pivaloyloxymethyl 6-(D-2-amino-2-[4-hydroxyphenyl]acetamido)penicillanate,
1-(ethoxycarbonyloxy)ethyl 6-(2-phenylacetamido)penicillanate,
1-(ethoxycarbonyloxy)ethyl 6-(D-2-amino-2-phenylacetamido)-penicillanate,
1-(ethoxycarbonyloxy)ethyl 6-(D-2-amino-2-[4-hydroxyphenyl]-acetamido)penicillanate,
3-phthalidyl 6-(2-phenylacetamido)penicillanate,
3-phthalidyl 6-(D-2-amino-2-phenylacetamido)penicillanate,
3-phthalidyl 6-(D-2-amino-2-[4-hydroxyphenyl]acetamido)penicillanate, 6-(2-phenoxycarbonyl-2-phenylacetamido)penicillanic acid,
6-(2-tolyloxycarbonyl-2-phenylacetamido)penicillanic acid,
6-(2-[5-indanyloxycarbonyl]-2-phenylacetamido)-penicillanic acid,
6-(2-phenoxycarbonyl-2-[3-thienyl]acetamido)penicillanic acid,
6-(2-tolyloxycarbonyl-2-[3-thienyl]acetamido)penicillanic acid,
6-(2-[5-indanyloxycarbonyl]-2-[3-thienyl]acetamido)-penicillanic acid,
6-(2,2-dimethyl-5-oxo-4-phenyl-1-imidazolidinyl)-penicillanic acid,
6-(D-2-[3-furfurylidineamino-2-oxoimidazolidine-1-carboxamido]-2-[4-hydroxyphenyl]acetamido)penicillanic acid,
7-(D-2-formyloxy-2-phenylacetamido)-3-([1-methyl-5-tetrazolyl]thiomethyl)-3-desacetoxymethylcephalosporanic acid,
7-(D-2-amino-2-phenylacetamido)-3-chloro-desacetoxymethylcephalosporanic acid,
7-(D-2-amino-2-[4-hydroxyphenyl]acetamido)-desacetoxycephalosporanic acid,
7-(2-[2-amino-4-thiazolyl]-2-[methoxyimino]acetamido)cephalosproanic acid,
7-(2-[2-thienyl]acetamido)cephalosporanic acid,
7-(2-[1-tetrazolyl]acetamido-3-([5-methyl-1,3,4-thiadiazoly-2-yl]thiomethyl)-3-desacetoxymethylcephalosporanic acid,
7-(D-2-amino-2-phenylacetamido)desacetoxycephalosporanic acid,
7-alpha-methoxy-7-(2-[2-thienyl]acetamido)-3-carbamoyloxymethyl-3-desacetoxymethylcephalosporanic acid,
7-(2-cyanoacetamido)cephalosporanic acid,
7-(D-2-hydroxy-2-phenylacetamido)-3-([1-methyl-5-tetrazolyl]thiomethyl)-3-desacetoxymethylcephalosporanic acid,
7-(2-[4-pyridylthio]acetamido)cephalosporanic acid,
7-(D-2-amino-2-[1,4-cyclohexadienyl]acetamido)cephalosporanic acid,
7-(D-2-amino-2-phenylacetamido)cephalosporanic acid,
7-(D-2-[4-ethylpiperazin-2,3-dione-1-carboxamido]-2-[4-hydroxyphenyl]acetamido)-3-([1-methyl-5-tetrazolyl]thiomehyl)-3-desacetoxymethylcephalosporanic acid, and
the pharmaceutically-acceptable salts thereof.

As will be appreciated by one skilled in the art, some of the above β-lactam compounds are effective when administered orally or parenterally, while others are effective only when administered by the parenteral route. When a compound of formula I, or a salt or an ester thereof readily hydrolyzable in vivo, is to be used simultaneously (i.e. co-mingled) with a β-lactam antibiotic which is effective only on parenteral administration, a combination formulation suitable for parenteral use will be required. When the compound of formula I or salt or ester thereof is to be used simultaneously (co-mingled) with a β-lactam antibiotic which is effective orally or parenterally, combinations suitable for either oral or parenteral administration can be prepared. Additionally, it is possible to administer preparations of the compound of formula I or salt or ester thereof orally, while at the same time administering a further β-lactam antibiotic parenterally; and it is also possible to administer preparations of the compound of formula I or salt or ester thereof parenterally, while at the same time administering the further β-lactam antibiotic orally.

The following examples are provided solely for the purpose of further illustration. Infrared (IR) spectra were measured as potassium bromide discs (KBr discs), and diagnostic absorption bands are reported in wave numbers (cm$^{-1}$). Nuclear magnetic resonance spectra (NMR) were measured at 60 MHz for solutions in deuterochloroform (CDCl$_3$) or perdeutero dimethyl sulfoxide (DMSO-d$_6$), and peak positions are expressed in parts per million (ppm) downfield from tetramethylsilane. The following abbreviations for peak shapes are used: s, singlet; d, doublet; q, quartet; m, multiplet.

EXAMPLE 1

2β-Acetoxymethyl-2α-methyl-(5R)penam-3α-carboxylic Acid 1,1-Dioxide

To a solution of 6.51 g. (41 mmole) of potassium permanganate in 130 ml. of water and 4.95 ml. of glacial acetic acid, cooled to ca. 5° C., is added to a cold (ca 5° C.) solution of 5.90 g. (21 mmole) of sodium salt of 2β-acetoxymethyl-2α-methyl-(5R)penam-3-carboxylic acid in 50 ml. of water. The mixture is stirred at ca. 5° C. for 20 minutes and then the cooling bath is removed. Solid sodium bisulfite is added until the color of the potassium permanganate has been discharged, and then the mixture is filtered. To the aqueous filtrate is added half its volume of saturated sodium chloride solution, and then the pH is adjusted to 1.7. The acidic solution is extracted with ethyl acetate. The extracts are dried, and then evaporated in vacuo, to give the title product.

EXAMPLE 2

2β-Acetoxymethyl-2α-methyl-(5R)penam-3α-carboxylic Acid 1,1-Dioxide

A stirred solution of 2.59 g. of 2β-acetoxymethyl-2α-methyl-(5R)penam-3α-carboxylic acid in 50 ml. of chloroform is cooled in an ice-bath. To this solution is then added 8.0 g. of 85% 3-chloroperbenzoic acid, in portions, over a period of 30 minutes. Stirring is continued for 30 minutes at ca. 0° C., and then the reaction mixture is stirred for 18 hours without cooling. The chloroform is removed by evaporation in vacuo, and the residue is slurried in 30 ml. of ether. The solid is recovered by filtration, washed with ether and dried, to give the title compound.

EXAMPLE 3

Pivaloyloxymethyl 2β-Acetoxymethyl-2α-methyl-(5R)penam-3α-carboxylate 1,1-Dioxide A stirred solution of 3.73 g. of pivaloyloxymethyl 2β-acetoxymethyl-2α-methyl-(5R)penam-3α-carboxylate in 40 ml. of chloroform is cooled in an ice-bath. To the solution is then added 8.0 g. of 85% pure 3-chloroperbenzoic acid in portions over a 15 minute period. Stirring is continued at ca. 0° C. for 30 minutes, and then the cooling bath is removed and stirring is continued for 16 hours. The reaction mixture is then cooled back to 0° C., and 70 ml. of water and 70 ml. of ethyl acetate are added. The organic layer is removed, and then it is washed successively with aqueous sodium sulfite solution, saturated aqueous sodium bicarbonate solution and saturated aqueous sodium chloride solution. The dried (Na$_2$SO$_4$) organic layer is evaporated in vacuo to give the title compound.

EXAMPLE 4

Oxidation of the 2β-acetoxymethyl-2α-methyl-(5R)penam-3α-carboxylate esters from Example 12 with 85% 3-chloroperbenzoic acid, according to the procedure of Example 3, affords the following compounds:

3'-phthalidyl 2β-acetoxymethyl-2α-methyl-(5R)penam-3α-carboxylate 1,1-dioxide,
4'-crotonolactonyl 2β-acetoxymethyl-2α-methyl-(5R)penam-3α-carboxylate 1,1-dioxide,
γ-butyrolacton-4'-yl 2β-acetoxymethyl-2α-methyl-(5R)penam-3α-carboxylate 1,1-dioxide,
acetoxymethyl 2β-acetoxymethyl-2α-methyl-(5R)penam-3α-carboxylate 1,1-dioxide,
hexanoyloxymethyl 2β-acetoxymethyl-2α-methyl-(5R)penam-3α-carboxylate 1,1-dioxide,
1'-(acetoxy)ethyl 2β-acetoxymethyl-2α-methyl-(5R)penam-3α-carboxylate 1,1-dioxide,
1'-(isobutyryloxy)ethyl 2β-acetoxymethyl-2α-methyl-(5R)penam-3α-carboxylate 1,1-dioxide,
1'-(2-methylvaleryloxy)ethyl 2β-acetoxymethyl-2α-methyl-(5R)penam-3α-carboxylate 1,1-dioxide,
1'-methyl-1'-(acetoxy)ethyl 2β-acetoxymethyl-2α-methyl-(5R)penam-3α-carboxylate 1,1-dioxide,
1'-methyl-1'-(hexanoyloxy)ethyl 2β-acetoxymethyl-2α-methyl-(5R)penam-3α-carboxylate 1,1-dioxide,
methoxycarbonyloxymethyl 2β-acetoxymethyl-2α-methyl-(5R)penam-3α-carboxylate 1,1-dioxide,
propoxycarbonyloxymethyl 2β-acetoxymethyl-2α-methyl-(5R)penam-3α-carboxylate 1,1-dioxde,
1'-(ethoxycarbonyloxy)ethyl 2β-acetoxymethyl-2α-methyl-(5R)penam-3α-carboxylate 1,1-dioxide,
1'-(butoxycarbonyloxy)ethyl 2β-acetoxymethyl-2α-methyl-(5R)penam-3α-carboxylate 1,1-dioxide,
1'-methyl-1'-(methoxycarbonyloxy)ethyl 2β-acetoxymethyl-2α-methyl-(5R)penam-3α-carboxylate 1,1-dioxide,
1'-methyl-1'-(ethoxycarbonyloxy)ethyl 2β-acetoxymethyl-2α-methyl-(5R)penam-3α-carboxylate 1,1-dioxide and
1'-methyl-1'-(hexanoyloxycarbonyloxy)ethyl 2β-acetoxymethyl-2α-methyl-(5R)penam-3β-carboxylate 1,1-dioxide

EXAMPLE 5

Benzyl 2β-Acetoxymethyl-2α-methyl-(5R)penam-3α-carboxylate 1,1-Dioxide

A stirred solution of 3.49 g. of benzyl 2β-acetoxymethyl-2α-methyl-(5R)penam-3α-carboxylate in 35 ml. of chloroform was cooled to 0° C., and 5 g. of 85% pure 3-chloroperbenzoic acid was added in two portions 15 minutes apart. The cooling bath was removed, and the mixture was stirred overnight without cooling. The reaction mixture was then cooled back to 0° C., and 70 ml. of water and 70 ml. of ethyl acetate were added. The organic layer was removed, and then it was washed successively with aqueous sodium sulfite solution, saturated aqueous sodium bicarbonate solution and saturated aqueous sodium chloride solution. The dried (Na$_2$SO$_4$) organic layer was evaporated in vacuo to give 4.8 g. of a brown oil, which slowly crystallized.

The above product was dissolved in 35 ml. of chloroform, and it was further oxidized using 5 g. of 85% 3-chloroperbenzoic acid for 19 hours. The reaction mixture was worked up as previously to give the crude title product. This crude product was dissolved in dichloromethane and the solution was washed with saturated aqueous sodium bicarbonate. Magnesium sulfate and decolorizing carbon were added to the dichloromethane solution, and then the filtered dichloromethane solution was evaporated in vacuo. This afforded 3.0 g. (79% yield) of the title compound. The NMR spectrum (CDCl$_3$) of the product showed absorptions at 1.25 (s, 3H), 2.00 (s, 3H), 3.40 (d, 2H), 4.55 (m, 4H), 5.15 (s, 2H) and 7.30 (s, 5H) ppm.

EXAMPLE 6

2β-Acetoxymethyl-2α-methyl-(5R)-penam-3α-carboxylic Acid 1,1-Dioxide

To a solution of 84.5 g. of benzyl 2β-acetoxymethyl-2α-methyl-(5R)penam-3α-carboxylate 1,1-dioxide in 1.1 liters of ethyl acetate was added 44 g. of 5% palladium-on-carbon. The mixture was shaken under an atmosphere of hydrogen at ca. 50 psig for 2 hours, and then the catalyst was removed by filtration.

The above filtrate was combined with the corresponding filtrate from a duplicate experiment, and the volume was reduced to 1.5 liters. To this solution was added, slowly, 1.7 liters of hexane. The volume was reduced to ca. 2 liters, and the solid which precipitated was recovered by filtration and slurried under hexane to give 98 g., (76% yield) of the title product. The NMR spectrum (CDCl$_3$+DMSO-d$_6$) showed absorptions at 1.65 (s, 3H), 2.15 (s, 3H), 3.55 (d, 2H) and 4.65 (m, 4H) ppm. The IR spectrum of the product (KBr disc) showed absorptions at 1785, 1330, 1225 and 1190 cm.$^{-1}$.

Analysis: Calcd. for C$_{10}$H$_{13}$NO$_7$S: C, 41.2; H, 4.49; N, 4.80; S, 11.00%. Found: C, 41.34; H, 4.55; N, 4.81; S, 11.08%.

EXAMPLE 7

Benzyl 2β-Acetoxymethyl-2α-methyl-(5R)penam-3α-carboxylate

A mixture of 68 ml. of acetic anhydride and 10 ml. of toluene was heated to 112° C. in a round bottom flask equipped with a distillation head and a condenser in the distillation position. When the temperature reached 112° C. liquid began to distil and then preheated toluene (ca. 100° C.) was added to the round bottom flask at the same rate that distillate was being collected. Slow distillation, and addition of preheated toluene, were continued for 20 minutes. At this point 10 g. of benzyl 2,2-dimethyl-(5R)penam-3α-carboxylate 1α-oxide was added to the liquid in the round bottom flask. A solution was obtained immediately. Slow distillation of the solution in the round bottom flask, and addition of preheated toluene, were continued for an additional 15 minutes. Throughout all this procedure, the temperature in the round bottom flask was maintained at 112° C. At this point the liquid in the round bottom flask was cooled to room temperature, and then it was evaporated in vacuo. This afforded a brown oil, which was partitioned between 100 ml. of ethyl acetate and 100 ml. of water. The pH of the aqueous phase was adjusted to 7.9 and the organic layer was removed. The organic layer was washed successively with water and saturated aqueous sodium chloride, and then it was dried and decolorized, using sodium sulfate and decolorizing carbon. Evaporation in vacuo gave 10.1 g. of crude title product.

EXAMPLE 8

Benzyl 2β-Acetoxymethyl-2α-methyl-(5R)penam-3α-carboxylate

The procedure of Example 7 was repeated on a ten times scale, except that the internal temperature was maintained at 115° C. after the benzyl ester had been added, and the heating was continued for 1 hour after the benzyl ester had been added. The yield of crude title compound was 122 g.

The product of this example was combined with that from Example 7, and then it was chromatographed on 4 kg. of silica gel. The column was eluted with 1:9 ethyl acetate-chloroform, taking 500 ml. fractions. The chromatography was followed by thin-layer chromatography and several fractions were combined to give 3 major cuts. Cut 1 was 7.0 g. of an ol and it was discarded. Cut 2 was 67.5 g. of a solid which was substantially pure title product. Cut 3 was 21.7 g. of a solid which was also substantially pure title product. The combination of cut 2 and 3 represents a 72% yield.

Cut 2 was dissolved in 450 ml. of isopropyl alcohol at 60° C. The solution was allowed to cool slowly, and then the product was collected by filtration. The recovery of recrystallized material was 34.1 g. The NMR spectrum of this material ($CDCl_3$) showed absorptions at 1.30 (s, 3H), 2.10 (s, 3H), 3.05 (d of d, 1H), 3.55 (d of d, 1H), 4.05 (q, 2H), 4.80 (s, 1H), 5.20 (s, 2H), 5.30 (m, 1H) and 7.30 (s, 5H) ppm.

EXAMPLE 9

Benzyl 2β-Acetoxymethyl-2α-methyl-(5R)penam-3α-carboxylate

The procedure of Example 7 is repeated, except that the benzyl 2,2-dimethyl-(5R)penam-3α-carboxylate 1α-oxide is replaced by an equal amount of benzyl 2,2-dimethyl-(5R)penam-3-carboxylate 1β-oxide. This affords benzyl 2β-acetoxymethyl-2α-methyl-(5R)penam-3α-carboxylate.

EXAMPLE 10

Benzyl 2β-Acetoxymethyl-2α-methyl-(5R)penam-3α-carboxylate

A solution of 31 g. of benzyl 2,2-dimethyl-(5R)penam-3α-carboxylate 1α-oxide in 210 ml. of acetic anhydride and 320 ml of toluene was heated to the boiling point. Liquid was allowed to distil off slowly, and toluene was added dropwise to maintain a constant volume in the reaction vessel. After 30 minutes, a sample was removed and examined by NMR spectroscopy. This showed that the reaction mixture contained benzyl 2,2-dimethyl-(5R)penam-3α-carboxylate 1α-oxide, benzyl 2,2-dimethyl-(5R)penam-3α-carboxylate 1β-oxide and benzyl 2β-acetoxymethyl-2α-methyl-(5R)penam-3α-carboxylate, in a ratio of approximately 1:4:4. The slow distillation and addition of fresh toluene was continued for an additional 25 minutes, and then the reaction mixture was cooled to room temperature. The solvents were removed by evaporation in vacuo. The residue was partitioned between water and ethyl acetate. The pH of the aqueous layer was adjusted to 3.0 and the layers were stirred for 15 minutes. The pH was raised to 8.0 and the layers were separated. The organic layer was washed successively with water at pH 8.0 and saturated aqueous sodium chloride, and then it was dried using sodium sulfate. Evaporation in vacuo of the organic layer afforded an oil, which was purified by column chromatograph on silica gel using 9:1 ethyl acetate-chloroform as the eluent. The column was monitored by thin-layer chromatography, and the fractions which appeared to contain substantially pure product were combined and evaporated. This afforded 17 g. of the title compound. A small sample of this material was slurried under ether and recovered by filtration as a white solid.

Analysis: Calcd. for $C_{17}H_{19}NO_5S$: C, 58.40; H, 5.48; N, 4.01. Found: C, 58.38; H, 5.55; N, 3.99%.

The earlier column fractions were rechromatographed, and the additional product obtained was combined with the material obtained above. The combined material was slurried with ether to give a final weight of 18 g. (50% yield) of benzyl 2β-acetoxymethyl-2α-methyl-(5R)penam-3α-carboxylate.

EXAMPLE 11

Pivaloyloxymethyl 2β-Acetoxymethyl-2α-methyl-(5R)penam-3α-carboxylate

The procedure of Exampe 7 is repeated, except that the benzyl 2,2-dimethyl-(5R)penam-3α-carboxylate 1α-oxide is replaced by an equal amount of pivaloyloxymethyl 2,2-dimethyl-(5R)penam-3α-carboxylate 1α-oxide. This affords the title compound.

EXAMPLE 12

Rearrangement of each of the 2,2-dimethyl-(5R)-penam-3α-carboxylate ester 1-oxides from Preparation H with acetic anhydride in toluene, according to the procedure of Example 7, affords the corresponding 2β-acetoxymethyl-2α-methyl-(5R)penam-3α-carboxylate ester. In this manner, the following compounds are prepared:

3'-phthalidyl 2β-acetoxymethyl-2α-methyl-(5R)penam-3α-carboxylate,

4'-crotonolactonyl 2β-acetoxymethyl-2α-methyl-(5R)-penam-3α-carboxylate,

γ-butyrolacton-4'-yl 2β-acetoxymethyl-2α-methyl-(5R)penam-3α-carboxylate, acetoxymethyl 2β-acetoxymethyl-2α-methyl-(5R)penam-3α-carboxylate, hexanoyloxymethyl 2β-acetoxymethyl-2α-methyl-(5R)penam-3α-carboxylate, 1'-(acetoxy)ethyl 2β-acetoxymethyl-2α-methyl-(5R)penam-3α-carboxylate, 1'-(isobutyryloxy)ethyl 2β-acetoxymethyl-2α-methyl-(5R)penam-3α-carboxylate, 1'-(2-methylvaleryloxy)ethyl 2β-acetoxymethyl-2α-methyl-(5R)penam-3α-carboxylate, 1'-methyl-1'-(acetoxy)ethyl 2β-acetoxymethyl-2α-methyl-(5R)penam-3α-carboxylate, 1'-methyl-1'-(hexanoyloxy)ethyl 2β-acetoxymethyl-2α-methyl-(5R)penam-3α-carboxylate, methoxycarbonyloxymethyl 2β-acetoxymethyl-2α-methyl-(5R)penam-3α-carboxylate, propoxycarbonyloxymethyl 2β-acetoxymethyl-2α-methyl-(5R)penam-3α-carboxylate, 1'-(ethoxycarbonyloxy)ethyl 2β-acetoxymethyl-2α-methyl-(5R)penam-3α-carboxylate, 1'-(butoxycarbonyloxy)ethyl 2β-acetoxymethyl-2α-methyl-(5R)penam-3α-carboxylate, 1'-methyl-1'-(methoxycarbonyloxy)ethyl 2β-acetoxymethyl-2α-methyl-(5R)penam-3α-carboxylate, 1'-methyl-1'-(ethoxycarbonyloxy)ethyl 2β-acetoxymethyl-2α-methyl-(5R)penam-3α-carboxylate and 1'-methyl-1'-(hexanoyloxycarbonyloxy)ethyl 2β-acetoxymethyl-2α-methyl-(5R)penam-3α-carboxylate.

EXAMPLE 13

2β-Acetoxymethyl-2α-methyl-(5R)penam-3α-carboxylic Acid

To a solution of 5 g. of benzyl 2β-acetoxymethyl-2α-methyl-(5R)penam-3α-carboxylate in 60 ml. of ethyl acetate is added 5 g. of 5% palladium-on-carbon. The mixture is shaken under an atmosphere of hydrogen at ca. 50 psig for 2 hours, and then the catalyst is removed by filtration. To the filtrate is added 100 ml. of water, and the pH of the aqueous phase is adjusted to 7.5. The aqueous layer is removed and it is covered with fresh ethyl acetate. The pH of the aqueous layer is reduced to 2.0 and the organic layer is removed. The organic layer is washed with water, and dried, and then it is evaporated in vacuo to give the title compound.

EXAMPLE 14

Pivaloyloxymethyl 2β-Acetoxymethyl-2α-methyl-(5R)penam-3α-carboxylate 1,1-Dioxide To a stirred solution of 2.92 g. of 2β-acetoxymethyl-2α-methyl-(5R)penam-3α-carboxylic acid 1,1-dioxide in 15 ml. of N,N-dimethylformamide is added 1.30 g. of diisopropylethylamine followed by 1.51 g. of chloromethyl pivalate and 50 mg. of sodium iodide at ca. 0° C. The reaction mixture is stirred at ca 0° C. for 30 minutes and then at room temperature for 24 hours. The reaction mixture is then diluted with ethyl acetate and water and the pH of the aqueous phase is adjusted to 7.5. The ethyl acetate layer is separated and washed three times with water and once with saturated sodium chloride solution. The ethyl acetate solution is then dried using anhydrous sodium sulfate, and evaporated in vacuo to give the title compound.

EXAMPLE 15

Reaction of sodium 2β-acetoxymethyl-2α-methyl-(5R)penam-3α-carboxylate 1,1-dioxide with 3-phthalidyl chloride, 4-crotonolactonyl chloride, γ-butyrolacton-4-yl chloride or the requisite alkanoyloxymethyl chloride, 1-(alkanoyloxy)ethyl chloride, 1-methyl-1-(alkanoyloxy)-ethyl chloride, alkoxycarbonyloxymethyl chloride, 1-(alkoxycarbonyloxy)ethyl chloride or 1-methyl-1-(alkoxycarbonyloxy)ethyl chloride, according to the procedure of Example 14, affords the following compounds:

3'-phthalidyl 2β-acetoxymethyl-2α-methyl-(5R)penam-3α-carboxylate 1,1-dioxide,

4'-crotonolactonyl 2β-acetoxymethyl-2α-methyl-(5R)penam-3α-carboxylate 1,1-dioxide, γ-butyrolacton-4'-yl 2β-acetoxymethyl-2α-methyl-(5R)-penam-3α-carboxylate 1,1-dioxide, acetoxymethyl 2β-acetoxymethyl-2α-methyl-(5R)-penam-3α-carboxylate 1,1-dioxide, hexanoyloxymethyl 2β-acetoxymethyl-2α-methyl-(5R)-penam-3α-carboxylate 1,1-dioxide, 1'-(acetoxy)ethyl 2β-acetoxymethyl-2α-methyl-(5R)penam-3α-carboxylate 1,1-dioxide, 1'-(isobutyryloxy)ethyl 2β-acetoxymethyl-2α-methyl-(5R)penam-3α-carboxylate 1,1-dioxide, 1'-methyl-1'-(acetoxy)ethyl 2β-acetoxymethyl-2α-methyl-(5R)penam-3α-carboxylate 1,1-dioxide, 1'-methyl-1'-(hexanoyloxy) 2β-acetoxymethyl-2α-methyl-(5R)penam-3α-carboxylate 1,1-dioxide, methoxycarbonyloxymethyl 2β-acetoxymethyl-2α-methyl-(5R)penam-3α-carboxylate 1,1-dioxide, propoxycarbonyloxymethyl 2β-acetoxymethyl-2α-methyl-(5R)penam-3α-carboxylate 1,1-dioxide, hexyloxycarbonyloxymethyl 2β-acetoxymethyl-2α-methyl-(5R)penam-3α-carboxylate 1,1-dioxide, 1'-(ethoxycarbonyloxy)ethyl 2β-acetoxymethyl-2α-methyl-(5R)penam-3α-carboxylate 1,1-dioxide, 1'-(butoxycarbonyloxy)ethyl 2β-acetoxymethyl-2α-methyl-(5R)penam-3α-carboxylate, 1,1-dioxide, 1'-methyl-1'-(methoxycarbonyloxy)ethyl 2β-acetoxymethyl-2α-methyl-(5R)penam-3α-carboxylate 1,1-dioxide and 1'-methyl-1'-(hexyloxycarbonyloxy)ethyl 2β-acetoxymethyl-2α-methyl-(5R)penam-3α-carboxylate 1,1-dioxide.

EXAMPLE 16

Sodium 2β-Acetoxymethyl-2α-methyl-(5R)-penam-3α-carboxylate 1,1-Dioxide

To a stirred suspension of 50 g. of 2β-acetoxymethyl-2α-methyl(5R)penam-3α-carboxylic acid 1,1-dioxide in 1,000 ml. of water was added 1 N sodium hydroxide until a stable pH of 5.0 was obtained. The aqueous solution so obtained was lyophilized to give 50 g. (92% yield) of the title sodium salt, $[\alpha]_D^{25} = 109.4$ ($H_2O$, c=1). The NMR spectrum (DMSO-$d_6$) showed absorptions 1.50 (s, 3H), 2.10 (s, 3H), 3.35 (q, 2H), 3.90 (s, 1H), 4.55 (q, 2H) and 5.00 (m, 1H). The IR spectrum (KBr disc) showed absorptions at 1785, 1625, 1325 and 1240 $cm^{-1}$.

PREPARATION A

Benzyl 2,2-Dimethyl-(5R)penam-3α-carboxylate 1α-Oxide

To a solution of 1756 g. of benzyl 6,6-dibromo-2,2-dimethyl-(5R)penam-3α-carboxylate 1α-oxide in 13.2 liters of tetrahydrofuran was added 9.4 liters of water, followed by 755 g. of potassium bicarbonate and 1756 g. of 5% palladium-on-calcium carbonate. This mixture was shaken under an atmosphere of hydrogen at ca. 50 psig for 1 hour. At this point the reaction mixture was diluted with 3.8 liters of ethyl acetate and 3.8 liters of water, and then it was filtered. The filter cake was washed with ethyl acetate and the ethyl acetate was added to the filtrate. The organic layer was removed, and then it was washed with 7 liters of water followed by 7 liters of saturated aqueous sodium chloride solution. The organic solution was dried using 450 g. of sodium sulfate and 280 g. of decolorizing carbon, and then it was evaporated in vacuo giving 833 g. (72% yield) of the title compound. The NMR spectrum ($CDCl_3$) showed absorptions at 1.35 (s, 3H), 1.60 (s, 3H9, 3.50 (m, 2H), 4.50 (s, 1H), 4.65 (m, 1H), 5.25 (s, 2H) and 7.40 (s, 5H) ppm.

PREPARATION B

Benzyl 6,6-Dibromo-2,2-dimethyl-(5R)penam-3α-carboxylate 1α-Oxide

A stirred solution of 1777 g. of benzyl 6,6-dibromo-2,2-dimethyl-(5R)penam-3α-carboxylate in 7.5 liters of chloroform, under nitrogen, was cooled to 0° C. To this solution was then added, portionwise during 35 minutes, 796 g. of 85% pure 3-chloroperbenzoic acid. The temperature was maintained at 0° C. throughout the addition. Stirring was continued at 0° C. for 15 minutes, and then the reaction mixture was stirred overnight without cooling. At this point the solid which had precipitated was removed by filtration, and the chloroform solution was washed three times with 3.7 liters of 5% aqueous sodium hydroxide. To the chloroform solution was then added 126 g. of decolorizing carbon. The mixture was stirred for 10 minutes, and then the carbon was removed by filtration. The chloroform solution was washed successively with water and saturated aqueous sodium chloride solution, and then it was dried using sodium sulfate. The chloroform solution was evaporated in vacuo at 25° to 29° C., to give 1756 g. (95% yield) of the title compound.

The NMR spectrum (CDCl$_3$) of a sample of the title compound obtained from an analogous experiment showed absorptions at 1.35 (s, 3H), 1.60 (s, 3H), 4.65 (s, 1H), 1.15 (m, 3H), 4.65 (s, 1H), 1.15 (m, 3H) and 7.55 (s, 5H) ppm.

PREPARATION C

Benzyl 6,6-Dibromo-2,2-dimethyl-(5R)penam-3-carboxylate

To a stirred solution of 1646 g. of 6,6-dibromo-2,2-dimethyl-(5R)penam-3α-carboxylic acid in 10.1 liters of N,N-dimethylacetamide was added 709 ml. of triethylamine during 10 minutes at ca. 0° C. The temperature was adjusted to 10° C., and 602 ml. of benzyl bromide was added during 4 minutes. To the reaction mixture was then added 941 g. of 4A molecular sieves, and then the reaction mixture was stirred overnight without external cooling. At this point, the reaction mixture was filtered and the filtrate was added to a mixture of 44 liters of ice-water and 14 liters of ethyl acetate. The pH of the aqueous phase was adjusted to 2.0 using 6 N hydrochloric acid, and the layers were separated. The aqueous layer was extracted with further ethyl acetate and the combined ethyl acetate solutions were washed sequentially with 14 liters of saturated, aqueous sodium bicarbonate and 14 liters of saturated, aqueous sodium chloride. The ethyl acetate solution was dried (Na$_2$SO$_4$), and then it was evaporated in vacuo at 25° C. The residue was dissolved in 5.5 liters of isopropyl alcohol at 60° C., and then the isopropyl alcohol solution was cooled slowly with stirring. The solid which precipitated was recovered by filtration, washed with cold isopropyl alcohol and then air dried. This afforded 1777 g. (85% yield) of the title product. The NMR spectrum (CDCl$_3$) showed absorptions at 1.40 (s, 3H), 1.55 (s, 3H), 4.55 (s, 1H), 5.20 (s, 2H), 5.75 (s, 1H) and 7.35 (s, 5H) ppm.

A second crop weighing 110 g. was obtained from the isopropyl alcohol mother liquors.

PREPARATION D

Benzyl 2,2-Dimethyl-(5R)-penam-3α-carboxylate 1β-Oxide

The title compound is prepared by esterification of 2,2-dimethyl-(5R)penam-3α-carboxylic acid 1β-oxide with benzyl bromide, using the procedure of Preparation C.

PREPARATION E

2,2-Dimethyl-(5R)penam-3α-carboxylic Acid 1α-Oxide

To 1.4 g. of prehydrogenated 5% palladium-on-calcium carbonate in 50 ml. of water was added a solution of 1.39 g. of benzyl 6,6-dibromo-2,2-dimethyl-(5R)penam-3α-carboxylate 1α-oxide in 50 ml. of tetrahydrofuran. The mixture was shaken under an atmosphere of hydrogen at ca. 45 p.s.i. and 25° C. for 1 hour, and then it was filtered. The filtrate was evaporated in vacuo to remove the bulk of the tetrahydrofuran, and then the aqueous phase was extracted with ether. The ether extracts were evaporated in vacuo to give 0.5 g. of material which appeared to be largely benzyl 2,2-dimethyl-(5R)penam-3α-carboxylate 1α-oxide.

The above benzyl 2,2-dimethyl-(5R)penam-3α-carboxylate 1α-oxide was combined with a further 2.0 g. of benzyl 6,6-dibromo-2,2-dimethyl-(5R)penam-3α-carboxylate 1α-oxide was dissolved in 50 ml. of tetrahydrofuran. The solution was added to 4.0 g. of 5% palladium-on-calcium carbonate, in 50 ml. of water, and the resulting mixture was shaken under an atmosphere of hydrogen, at ca. 45 p.s.i. and 25° C. overnight. The mixture was filtered, and the filtrate was extracted with ether. The extracts were evaporated in vacuo and the residue was purified by chromatography on silica gel, eluting with chloroform. This afforded 0.50 g. of material.

The latter material was hydrogenated at ca. 45 p.s.i. at 25° C. in water-methanol (1:1) with 0.50 g. of 5% palladium-on-calcium carbonate for 2 hours. At this point, an additional 0.50 g. of 5% palladium-on-calcium carbonate was added and the hydrogenation was continued at 45 p.s.i. and 25° C. overnight. The reaction mixture was filtered, extracted with ether and the extracts were discarded. The residual aqueous phase was adjusted to pH 1.5 and then extracted with ethyl acetate. The ethyl acetate extracts were dried (Na$_2$SO$_4$) and then evaporated in vacuo to give 0.14 g. of the title compound. The NMR spectrum (CDCl$_3$/DMSO-d$_6$) showed absorptions at 1.4 (s, 3H), 1.64 (s, 3H), 3.60 (m, 2H), 4.3 (s, 1H) and 4.54 (m, 1H) ppm. The IR spectrum of the product KBr disc) showed absorptions at 1795 and 1745 cm$^{-1}$.

PREPARATION F

2,2-Dimethyl-(5R)penam-3α-carboxylic Acid 1β-Oxide

To a stirred suspension of 2.65 g. (12.7 mmole) of 2,2-dimethyl-(5R)penam-3α-carboxylic acid in chloroform at 0° C. was aded 2.58 g. of 85% pure 3-chloroperbenzoic acid. After 1 hour, the reaction mixture was filtered and the filtrate was evaporated in vacuo. The residue was dissolved in a small amount of chloroform. The solution was concentrated slowly until a precipitate began to appear. At this point the evaporation was stopped and the mixture was diluted with ether. The precipitate was removed by filtration, washed with ether and dried, to give 0.615 g. of penicillanic acid 1β-oxide, m.p. 140°-3° C. The IR spectrum of the product (CHCl₃ solution) showed absorptions at 1775 and 1720 cm⁻¹. The NMR spectrum (CDCl₃/DMSO-d₆) showed absorptions at 1.35 (s, 3H), 1.76 (s, 3H), 3.36 (m, 2H), 4.50 (s, 1H) and 5.05 (m, 1H) ppm. From the NMR spectrum, the product appeared to be ca. 90% pure.

Examination of the chloroform-ether mother liquor revealed that it contained further 2,2-dimethyl-(5R)penam-3α-carboxylic acid 1β-oxide, and also some 2,2-dimethyl-(5R)penam-3α-carboxylic acid 1α-oxide.

PREPARATION G

Pivaloyloxymethyl 2,2-Dimethyl-(5R)-penam-3α-carboxylate 1α-Oxide

To a stirred solution of 2.17 g. of 2,2-dimethyl-(5R)penam-3α-carboxylic acid 1α-oxide in 15 ml. of N,N-dimethylformamide is added 1.30 g. of diisopropylethylamine followed by 1.51 g. of chloromethyl pivalate and 50 mg. of sodium iodide at ca. 0° C. The reaction mixture is stirred at ca. 0° C. for 30 minutes and then at room temperature for 24 hours. The reaction mixture is then diluted with ethyl acetate and water and the pH of the aqueous phase is adjusted to 7.5. The ethyl acetate layer is separated and washed three times with water and once with saturated sodium chloride solution. The ethyl acetate solution is then dried using anhydrous sodium sulfate, and evaporated in vacuo to give the title compound.

PREPARATION H

Reaction of 2,2-dimethyl-(5R)penam-3α-carboxylic acid 1α-oxide or 2,2-dimethyl-(5R)penam-3α-carboxylic acid 1β-oxide, as appropriate, with 3-phthalidyl chloride, 4-crotonolactonyl chloride, γ-butyrolacton-4-yl chloride or the requisite alkanoyloxymethyl chloride, 1-(alkanoyloxy)ethyl chloride, 1-methyl-1-(alkanoyloxy)ethyl chloride, alkoxycarbonyloxymethyl chloride, 1-(alkoxycarbonyloxy)ethyl chloride or 1-methyl-1-(alkoxycarbonyloxy)ethyl chloride, according to the procedure of Preparation G, affords the following compounds:

3'-phthalidyl 2,2-dimethyl-(5R)penam-3α-carboxylate 1α-oxide,
3'-phthalidyl 2,2-dimethyl-(5R)-penam-3α-carboxylate 1β-oxide,
4'-crotonolactonyl 2,2-dimethyl-(5R)penam-3α-carboxylate 1α-carboxylate 1α-oxide,
γ-butyrolacton-4'-yl 2,2-dimethyl-(5R)penam-3α-carboxylate 1β-oxide,
acetoxymethyl 2,2-dimethyl-(5R)penam-3α-carboxylate 1α-oxide,
hexanoyloxymethyl 2,2-dimethyl-(5R)penam-3α-carboxylate 1α-oxide,
1'-(acetoxy)ethyl 2,2-dimethyl-(5R)penam-3α-carboxylate 1α-oxide,
1'-(acetoxy)ethyl 2,2-dimethyl-(5R)penam-3α-carboxylate 1α-oxide,
1'-(isobutyryloxy)ethyl 2,2-dimethyl-(5R)penam-3α-carboxylate 1β-oxide,
1'-(2-methylvaleryloxy)ethyl 2,2-dimethyl-(5R)penam-3α-carboxylate 1α-oxide,
1'-methyl-1'-(acetoxy)ethyl 2,2-dimethyl-(5R)penam-3α-carboxylate 1β-oxide,
1'-methyl-1'-(acetoxy)ethyl 2,2-dimethyl-(5R)penam-3α-carboxylate 1α-oxide,
1'-methyl-1'-(hexanoyloxy)ethyl 2,2-dimethyl-(5R)penam-3α-carboxylate 1β-oxide,
methoxycarbonyloxymethyl 2,2-dimethyl-(5R)penam-3α-carboxylate 1α-oxide,
propoxycarbonyloxymethyl 2,2-dimethyl-(5R)penam-3α-carboxylate 1β-oxide,
1'-(ethoxycarbonyloxy)ethyl 2,2-dimethyl-(5R)penam-3α-carboxylate 1α-oxide,
1'-(butoxycarbonyloxy)ethyl 2,2-dimethyl-(5R)penam-3α-carboxylate 1β-oxide,
1'-methyl-1'-(methoxycarbonyloxy)ethyl 2,2-dimethyl-(5R)-penam-3α-carboxylate 1α-oxide,
1'-methyl-1'-(ethoxycarbonyloxy)ethyl 2,2-dimethyl-(5R)-penam-3α-carboxylate 1β-oxide and
1'-methyl-(hexanoyloxycarbonyloxy)ethyl 2,2-dimethyl-(5R)penam-3α-carboxylate 1α-oxide.

I claim:

1. A penam compound of the formula

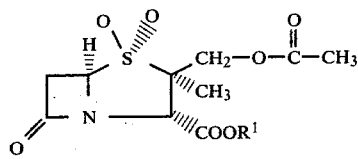

and the pharmaceutically-acceptable base salts thereof, wherein $R^1$ is selected from the group consisting of hydrogen 3-phthalidyl, 4-crotonolactonyl, gamma-butyrolacton-4-yl,

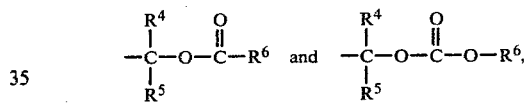

wherein $R^4$ and $R^5$ are each selected from the group consisting of hydrogen and methyl, and $R^6$ is alkyl having from 1 to 5 carbon atoms.

2. The compound according to claim 1, wherein $R^1$ is hydrogen.

3. A compound according to claim 1, wherein $R^1$ is selected from the group consisting of 3-phthalidyl, 4-crotonolactonyl, γ-butyrolacton-4-yl,

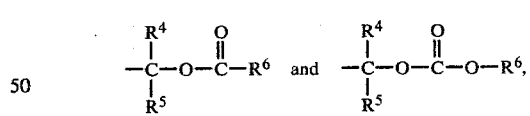

wherein $R^4$ and $R^5$ are each selected from the group consisting of hydrogen and methyl, and $R^6$ is alkyl having from 1 to 5 carbon atoms.

4. A compound according to claim 3, wherein $R^1$ is

wherein $R^4$ and $R^5$ are each hydrogen and $R^6$ is alkyl having from 1 to 5 carbon atoms.

5. The compound according to claim 4, wherein $R^6$ is t-butyl.

6. A compound according to claim 3, wherein $R_1$ is

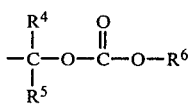

wherein R⁴ is hydrogen, R⁵ is methyl and R⁶ is alkyl having from 1 to 5 carbon atoms.

7. The compound according to claim 6, wherein R⁶ is ethyl.

8. A beta-lactam antibiotic effectiveness enhancing composition, which comprises a penam compound of the formula

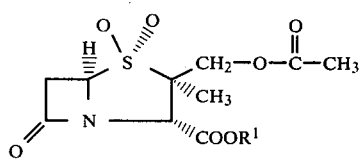

or a pharmaceutically-acceptable base salt thereof, and a pharmaceutically-acceptable carrier;
wherein
R¹ is selected from the group consisting of hydrogen, 3-phthalidyl, 4-crotonolactonyl, gamma-butyrolacton-4-yl,

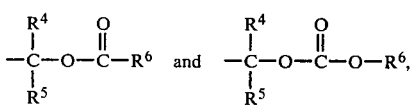

wherein
R⁴ and R⁵ are each selected from the group consisting of hydrogen and methyl, and R⁶ is alkyl having from 1 to 5 carbon atoms; and
wherein said penam compound is present in an amount in the range from 20 to 95 percent by weight.

9. A composition according to claim 8, wherein R¹ is hydrogen.

10. A method of increasing the effectiveness of a beta-lactam antibiotic in a human subject, which comprises coadministering with said beta-lactam antibiotic, to said human subject, a beta-lactam antibiotic effectiveness increasing amount of a penam compound of the formula

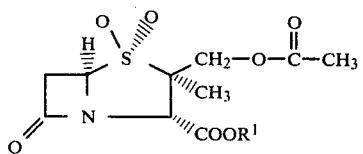

or a pharmaceutically-acceptable base salt thereof;
wherein
R¹ is selected from the group consisting of hydrogen, 3-phthalidyl, 4-crotonolactonyl, gamma-butyrolacton-4-yl,

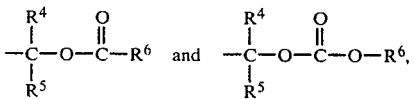

wherein
R⁴ and R⁵ are each selected from the group consisting of hydrogen and methyl, and R⁶ is alkyl having from 1 to 5 carbon atoms; and
wherein said beta-lactam antibiotic is selected from the group consisting of:
6-(2-phenylacetamido)penicillanic acid,
6-(2-phenoxyacetamido)penicillanic acid,
6-(2-phenylpropionamdio)penicillanic acid,
6-(D-2-amino-2-phenylacetamido)penicillanic acid,
6-(D-2-amino-2-[4-hydroxyphenyl]acetamido)-penicillanic acid,
6-(D-2-amino-2-[1,4-cyclohexadienyl]acetamido)-penicillanic acid,
6-(1-aminocyclohexanecarboxamido)penicillanic acid,
6-(2-carboxy-2-phenylacetamido)penicillanic acid,
6-(2-carboxy-2-[3-thienyl]acetamido)penicillanic acid,
6-(D-2-[4-ethylpiperazin-2,3-dione-1-carboxamido]-2-phenylacetamido)penicillanic acid,
6-(D-2-[4-hydroxy-1,5-naphthyridine-3-carboxamido]-2-phenylacetamido)pencillanic acid,
6-(D-2-sulfo-2-phenylacetamido)penicillanic acid,
6-(D-2-sulfoamino-2-phenylacetamido)penicillanic acid,
6-(D-2-[imidazolidin-2-one-1-carboxamido]-2-phenylacetamido)-penicillanic acid,
6-(D-[3-methylsulfonylimidazolidin-2-one-1-carboxamido]-2-phenylacetamido)penicillanic acid,
6-([hexahydro-1H- azepin-1-yl]methyleneamino)-penicillanic acid,
acetoxymethyl 6-(2-phenylacetamido)penicillanate,
acetoxymethyl 6-(D-2-amino-2-phenylacetamido)-penicillanate,
acetoxymethyl 6-(D-2-amino-2-[4-hydroxyphenyl]acetamido)-penicillanate,
pivaloyloxymethyl 6-(2-phenylacetamido)penicillanate,
pivaloyloxymethyl 6-(D-2-amino-2-phenylacetamido)penicillanate,
pivaloyloxymethyl 6-(D-2-amino-2-[4-hydroxyphenyl]acetamido)-penicillanate,
1-(ethoxycarbonyloxy)ethyl 6-(2-phenylacetamido)-penicillanate,
1-(ethoxycarbonyloxy)ethyl 6-(D-2-amino-2-phenylacetamido)-penicillanate,
1-(ethoxycarbonyloxy)ethyl 6-(D-2-amino-2-[4-hydroxyphenyl]-acetamido)penicillanate,
3-phthalidyl 6-(2-phenylacetamido)penicillanate,
3-phthalidyl 6-(D-2-amino-2-phenylacetamido)-penicillanate,
3-phthalidyl 6-(D-2-amino-2-[4-hydroxyphenyl]acetamido)penicillanate
6-(2-phenoxycarbonyl-2-phenylacetamido)penicillanic acid,
6-(2-tolyloxycarbonyl-2-phenylacetamido)penicillanic acid,
6-(2-[5-indanyloxycarbonyl]-2-phenylacetamido)-penicillanic acid,
6-(2-phenoxycarbonyl-2-[3-thienyl]acetamido)-penicillanic acid,
6-(2-tolyloxycarbonyl-2-[3-thienyl]acetamido)-penicillanic acid,
6-(2-[5-indanyloxycarbonyl]-2-[3-thienyl]acetamido)-penicillanic acid,
6-(2,2-dimethyl-5-oxo-4-phenyl-1-imidazolidinyl)-penicillanic acid, 6-(D-2-[3-furfurylidineamino-2-oxoimidazolidine-1-carboxamido]-2-[4-hydroxyphenyl]acetamido)penicillanic acid, 7-(D-2-formyloxy-2-phenylacetamido)-3-([1-methyl-5-tetrazolyl]-thiomethyl)-3-desacetoxymethylcephalosporanic acid, 7-(D-2-amino-2-phenylacetamido)-3-chloro-desacetoxymethylcephalosporanic acid, 7-(D-2-amino-2-[4-hydroxyphenyl]acetamido)-desacetoxycephalosporanic acid, 7-(2-[2-amino-4-thiazolyl]-2-[methoxyimino]acetamido)cephalosporanic acid, 7-(2-[2-thienyl]acetamido)cephalosporanic acid, 7-(2-[1-tetrazolyl]acetamido-3-([5-methyl-1,3,4-thiadiazol-2-yl]thiomethyl)-3-desacetoxymethylcephalosporanic acid, 7-(D-2-amino-2-phenylacetamido)desacetoxycephalosporanic acid, 7-alpha-methoxy-7-(2-[2-thienyl]acetamido)-3-carbamoyloxymethyl-3-desacetoxymethylcephalosporanic acid, 7-(2-cyanoacetamido)cephalosporanic acid, 7-(D-2-hydroxy-2-phenylacetamido)-3-([1-methyltetrazol-5-yl]-thiomethyl)-3-desacetoxymethylcephalosporanic acid, 7-(2-[4-pyridylthio]acetamido)cephalosporanic acid, 7-(D-2-amino-2-[1,4-cyclohexadiethyl]acetamido)cephalosporanic acid, 7-(D-2-amino-2-phenylacetamido)cephalosporanic acid, 7-(D-2-[4-ethylpiperazin-2,3-dione-1-carboxamido]-2-[4-hydroxyphenyl]acetamido)-3-([1-methyl-5-tetrazolyl]thiomethyl)-3-desacetoxymethylcephalosporanic acid, and the pharmaceutically-acceptable salts thereof.

11. A penam compound of the formula

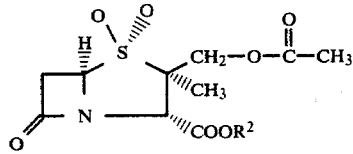

wherein $R^2$ is selected from the group consisting of tetrahydropyranyl, benzyl, 4-nitrobenzyl, benzylhydryl, 2,2,2-trichloroethyl, t-butyl and phenacyl.

12. A penam compound of the formula:

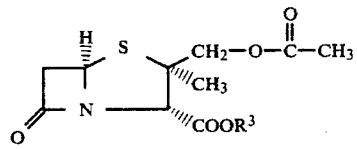

wherein $R^3$ is selected from the group consisting of hydrogen, tetrahydropyranyl, benzyl, 4-nitrobenzyl, benzhydryl, 2,2,2-trichloroethyl, t-butyl, phenacyl, 3-phthalidyl, 4-crotonolactonyl, gamma-butyrolacton-4-yl,

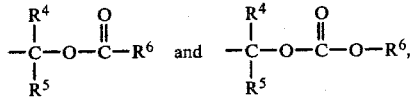

wherein $R^4$ and $R^5$ are each selected from the group consisting of hydrogen and methyl, and $R^6$ is alkyl having from 1 to 5 carbon atoms.

13. The method according to claim 10, wherei said β-lactam antibiotic is selected from the group consisting of:

6-(2-phenylacetamido)penicillanic acid,
6-(2-phenoxyacetamido)penicillanic acid,
6-(D-2-amino-2-phenylacetamido)penicillanic acid,
6-(D-2-amino-2-[4-hydroxyphenyl]acetamido)penicillanic acid,
6-(D-2-[4-ethylpiperazin-2,3-dione-1-carboxamido]-2-[4-hydroxyphenyl]acetamido)-3-([1-methyl-5-tetrazolyl]thiomethyl)-3-desacetoxymethylcephalosporanic acid, and the pharmaceutically-acceptable base salts thereof.

14. The method according to either claim 10 or claim 18, wherein $R^1$ is hydrogen.

15. The compound according to claim 11, wherein $R^2$ is benzyl.

16. The compound according to claim 12, wherein $R^3$ is hydrogen.

17. A compound according to claim 12, wherein $R^3$ is selected from the group consisting of 3-phthalidyl, 4-crotonolactonyl, γ-butyrolacton-4-yl,

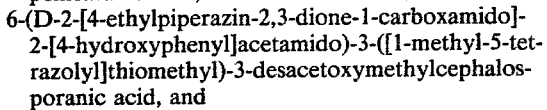

wherein $R^4$ and $R^5$ are each selected from the group consisting of hydrogen and methyl, and $R^6$ is alkyl having from 1 to 5 carbon atoms.

18. A compound according to claim 17, wherein $R^3$ is

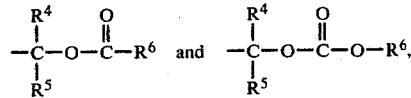

wherein $R^4$ and $R^5$ are each hydrogen and $R^6$ is alkyl having from 1 to 5 carbon atoms.

19. The compound according to claim 17, wherein $R^6$ is t-butyl.

20. A compound according to claim 17, wherein $R^3$ is

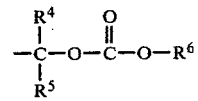

wherein $R^4$ is hydrogen, $R^5$ is methyl and $R^6$ is alkyl having from 1 to 5 carbon atoms.

21. The compound according to claim 20, wherein $R^6$ is ethyl.

22. The compound according to claim 12, wherein $R^1$ is benzyl.

* * * * *

UNITED STATES PATENT AND TRADEMARK OFFICE
CERTIFICATE OF CORRECTION

PATENT NO. : 4,256,733
DATED : MARCH 17, 1981
INVENTOR(S) : WAYNE E. BARTH

It is certified that error appears in the above-identified patent and that said Letters Patent are hereby corrected as shown below:

At column 26, line 24, cancel "18" and substitute -- 13 --.

Signed and Sealed this

Second Day of June 1981

[SEAL]

Attest:

RENE D. TEGTMEYER

Attesting Officer

Acting Commissioner of Patents and Trademarks